US00PP25896P2

(12) United States Plant Patent
Bulthouse

(10) Patent No.: US PP25,896 P2
(45) Date of Patent: Sep. 15, 2015

(54) ***BUXUS* PLANT NAMED 'BULTHOUSE'**

(50) Latin Name: ***Buxus microphylla* var. *koreana***
Varietal Denomination: Bulthouse

(71) Applicant: John Bulthouse, Norton Shores, MI (US)

(72) Inventor: John Bulthouse, Norton Shores, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 139 days.

(21) Appl. No.: 13/987,985

(22) Filed: Sep. 20, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — C. A. Whealy

(57) ABSTRACT

A new and distinct cultivar of Buxus plant named 'Bulthouse', characterized by its upright, mounded and uniform plant habit; freely branching habit; dense and bushy appearance; vigorous growth habit and relatively fast growth rate; emerald green-colored leaves; and good winter hardiness.

2 Drawing Sheets

Botanical designation: *Buxus microphylla* var. *koreana.*
Cultivar denomination: 'BULTHOUSE'.

BACKGROUND OF THE INVENTION

The present invention relates to a new and distinct *Buxus* plant, commercially produced as an ornamental shrub, botanically known as *Buxus microphylla* var. *koreana* and hereinafter referred to by the name 'Bulthouse'.

The new *Buxus* plant is a naturally-occurring branch mutation of *Buxus microphylla* var. *koreana* 'Winter Gem', not patented. The new *Buxus* plant was discovered and selected by the Inventor on a single plant of 'Winter Gem' in a controlled outdoor nursery environment in Norton Shores, Mich. in July, 2005.

Asexual reproduction of the new *Buxus* plant by hardwood cuttings in a controlled nursery environment in Norton Shores, Mich. since November, 2005 has shown that the unique features of this new *Buxus* plant are stable and reproduced true to type in successive generations.

SUMMARY OF THE INVENTION

Plants of the new *Buxus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Bulthouse'. These characteristics in combination distinguish 'Bulthouse' as a new and distinct *Buxus* plant:

1. Upright, mounded and uniform plant habit.
2. Freely branching habit; dense and bushy appearance.
3. Vigorous growth habit and relatively fast growth rate.
4. Emerald green-colored leaves.
5. Good winter hardiness.

Plants of the new *Buxus* differ primarily from plants of the mutation parent, 'Winter Gem', in the following characteristics:

1. Plants of the new *Buxus* are more upright than plants of 'Winter Gem'.
2. Plants of the new *Buxus* grow faster than plants of 'Winter Gem'.
3. Plants of the new *Buxus* do not produce flowers whereas plants of 'Winter Gem' produce flowers.

Plants of the new *Buxus* can be compared to plants of *Buxus microphylla* var. *koreana*×*Buxus sempervirens* 'Green Gem', not patented. In side-by-side comparisons conducted in Grand Haven, Mich., plants of the new *Buxus* differed from plants of 'Green Gem' in the following characteristics:

1. Plants of the new *Buxus* were more upright than plants of 'Green Gem'.
2. Plants of the new *Buxus* grew faster than plants of 'Green Gem'.
3. Plants of the new *Buxus* did not produce flowers whereas plants of 'Green Gem' produced flowers.

BRIEF DESCRIPTION OF THE PHOTOGRAPHS

The accompanying colored photographs illustrate the overall appearance of the new *Buxus* plant showing the colors as true as it is reasonably possible to obtain in colored reproductions of this type. Colors in the photographs may differ slightly from the color values cited in the detailed botanical description which accurately describe the colors of the new *Buxus* plant.

The photograph on the first sheet comprises a side perspective view of a typical plant of 'Bulthouse' grown in an container. po The photograph on the second sheet is a close-up view of a typical plant of 'Bulthouse'.

DETAILED BOTANICAL DESCRIPTION

The aforementioned photographs and following observations, measurements and values describe plants grown in one-gallon containers during the summer in an outdoor nursery in Grand Haven, Mich. Plants were two years old when the photographs and description were taken. In the following description, color references are made to The Royal Horticultural Society Colour Chart, 1995 Edition, except where general terms of ordinary dictionary significance are used.

Botanical classification: *Buxus microphylla* var. *koreana* 'Bulthouse'.

Parentage: Naturally-occurring branch mutation of *Buxus microphylla* var. *koreana* 'Winter Gem', not patented.

Propagation:

*Type*.—By hardwood cuttings.

*Time to initiate roots*.—About one month at 20° C.

*Time to produce a rooted young plant*.—About one year at 25° C.

*Root description*.—Thick and fine; cream and brown in color.

*Rooting habit*.—Freely branching; dense.

Plant description:

*Plant form and growth habit*.—Evergreen shrub with upright, mounding and uniform plant habit; freely branching habit, about numerous lateral branches developing per plant; dense and bushy appearance; vigorous growth habit and relatively rapid growth rate.

*Plant height*.—About 24 cm.

*Plant width* (*spread*).—About 20 cm.

*Lateral branches*.—Length: About 15 cm. Diameter: About 2 mm. Internode length: About 8 mm. Strength: Strong. Texture: Smooth, glabrous. Color: Close to 144A.

Leaf description:

*Arrangement*.—Opposite, simple.

*Length*.—About 2 cm.

*Width*.—About 1.2 cm.

*Shape*.—Broadly elliptic to obovate.

*Apex*.—Obtuse; occasionally slightly retuse.

*Base*.—Obtuse to cuneate.

*Margin*.—Entire.

*Texture, upper and lower surfaces*.—Rugose, glabrous.

*Venation pattern*.—Pinnate.

*Color*.—Developing leaves, upper surface: Close to 144A. Developing leaves, lower surface: Close to 144B. Fully expanded leaves, upper surface: Close to 132A; venation, close to 132A. Fully expanded leaves, lower surface: Close to 146C; venation, close to 146C.

*Petiole*.—Length: About 3 mm. Diameter: About 2 mm. Texture, upper and lower surfaces: Smooth, glabrous. Color, upper and lower surfaces: Close to 146B.

Flower description: Flower initiation and development has not been observed on plants of the new *Buxus*.

Disease & pest resistance: Plants of the new *Buxus* have not been noted to be resistant to pathogens and pests common to *Buxus*.

Temperature tolerance: Plants of the new *Buxus* have been observed to tolerate high temperatures of about 30° C. and to be hardy to USDA Hardiness Zone 5.

It is claimed:

1. A new and distinct *Buxus* plant named 'Bulthouse' as illustrated and described.

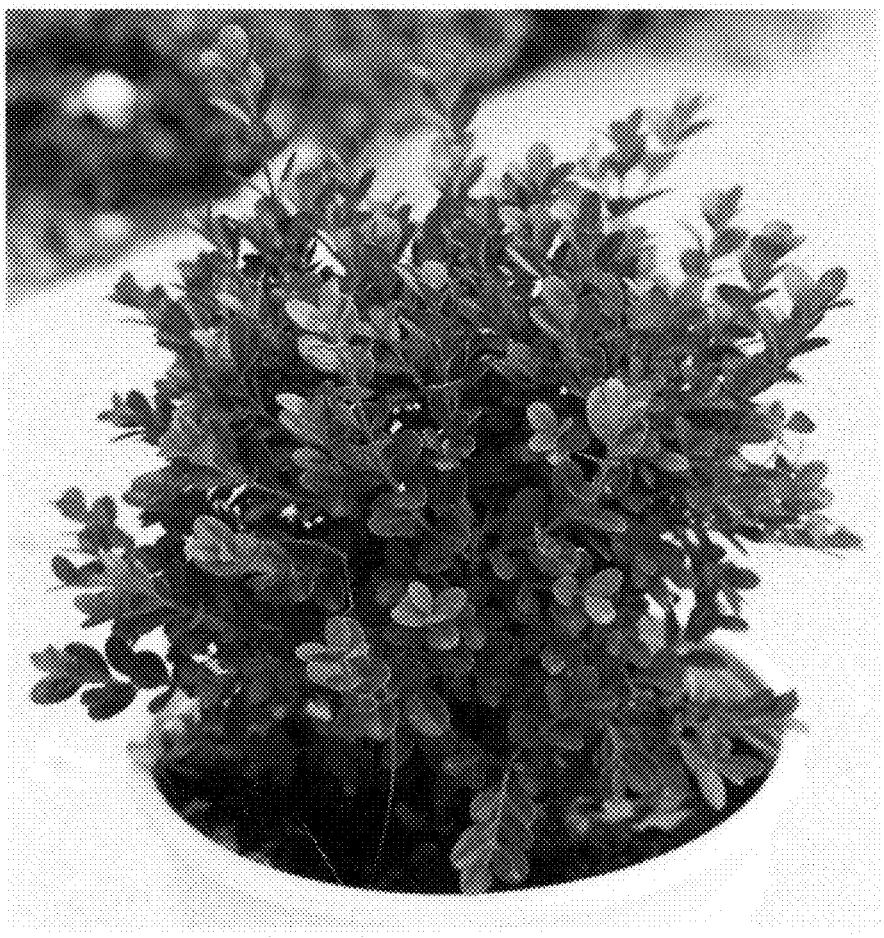

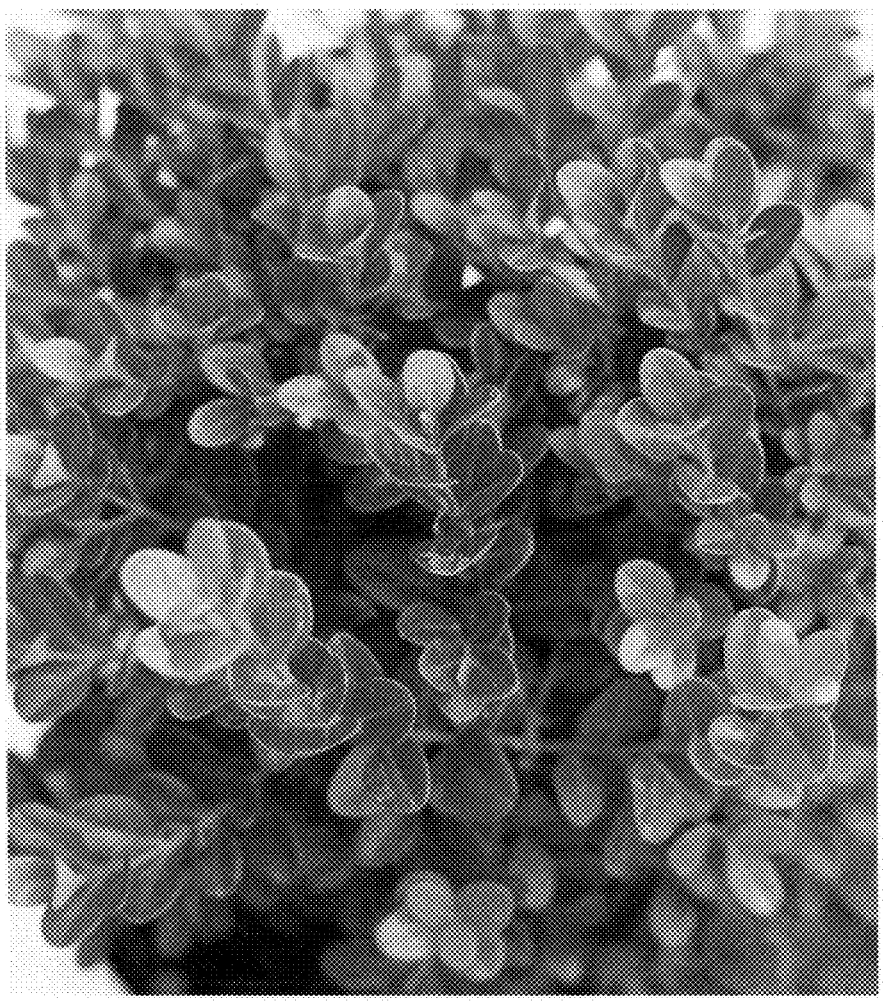

* * * * *